United States Patent [19]

Jaxa-Chamiec et al.

[11] Patent Number: 5,230,885
[45] Date of Patent: Jul. 27, 1993

[54] POLYSTYRENE ANION EXCHANGE POLYMER PHARMACEUTICAL COMPOSITION

[75] Inventors: Albert A. Jaxa-Chamiec, Rickmansworth; Deirdre M. B. Hickey, Welwyn, both of England

[73] Assignee: Smith Kline & French Laboratories Limited, Welwyn Garden City, England

[21] Appl. No.: 536,921

[22] Filed: Jun. 12, 1990

Related U.S. Application Data

[63] Continuation-in-part of Ser. No. 288,049, Dec. 21, 1988, Pat. No. 4,954,339.

[30] Foreign Application Priority Data

Dec. 23, 1987 [GB] United Kingdom ............... 8730010
Jun. 15, 1989 [GB] United Kingdom ............... 8913823

[51] Int. Cl.$^5$ .............................................. A61K 31/74
[52] U.S. Cl. .................................. 424/78.16; 521/31; 521/32
[58] Field of Search .............................. 424/79, 78.16

[56] References Cited

U.S. PATENT DOCUMENTS

| | | | |
|---|---|---|---|
| 3,780,171 | 12/1973 | Irmscher et al. | 424/79 |
| 3,898,088 | 8/1975 | Cohen et al. | 96/84 A |
| 4,198,395 | 4/1980 | De Simone | 424/79 |
| 4,311,799 | 1/1982 | Miyake et al. | 521/31 |
| 4,510,128 | 4/1985 | Khanna | 424/78 |
| 4,532,128 | 7/1985 | Sheldon et al. | 424/78 |

FOREIGN PATENT DOCUMENTS

| | | |
|---|---|---|
| 929391 | 6/1963 | United Kingdom . |
| 1286949 | 12/1969 | United Kingdom . |
| 2026501A | 2/1980 | United Kingdom . |

OTHER PUBLICATIONS

Walfish, et al., Water, Air & Soil Pollution 12:477-484 (1979).
Carpov, et al., J. Macromol. Sci. Chem., A22(5-7):907-929 (1985).
Takeuchi, et al., Chem. Pharm. Bull. 32(3):823-831 (1984).
Petrariu, et al., Revue Roumaine de Chimie, 25:145-154 (1980).
Wessling, et al., Makromol. Chem., suppl. 10/11:319-336 (1985).

*Primary Examiner*—Thurman K. Page
*Assistant Examiner*—Peter F. Kulkoski
*Attorney, Agent, or Firm*—Wayne J. Dustman; Stephen Venetianer; Edward T. Lentz

[57] ABSTRACT

Polystyrene polymers having a quaternised ammonium group and their use in a method of treatment of hypercholesterolaemia. A particular compound of the invention is (N,N-dimethyl-N-dodecyl-ammoniomethylstyrene-ethyl methacrylate-divinylbenzene co-polymer, chloride salt.

12 Claims, No Drawings

POLYSTYRENE ANION EXCHANGE POLYMER PHARMACEUTICAL COMPOSITION

This application is a continuation-in-part of U.S. Ser. No. 288,049 filed Dec. 21, 1988, now U.S. Pat. No. 4,954,339.

The present invention relates to novel polystyrene anion exchange polymers, processes for their preparation, intermediates useful in their preparation, pharmaceutical compositions containing them and their use in the lowering of plasma cholesterol levels in humans.

Coronary Heart Disease (CHD) is one of the most serious health problems of contemporary society. Worldwide epidemiological studies have shown that the incidence of CHD is related to a number of independent risk factors, in particular, for example, high concentrations of serum cholesterol (hypercholesterolaemia). Such adverse factors lead to atherosclerosis, and ultimately, in severe cases, intermittent claudication, cerebrovascular insufficiency, thrombosis and cardiac arrest.

It is known that ion exchange polymers, in particular polystyrene polymers can be used as sequestering agents to bind non-absorbed bile acids and salts in the intestinal tract, forming complexes which are then excreted in the faeces. This sequestering leads to a decrease in the amount of bile acids returning to the liver via enterohepatic circulation. The synthesis of replacement bile acids from hepatic cholesterol depletes hepatic cholesterol, regulates hepatic LDL receptors and consequently reduces plasma cholesterol levels. Such sequestering polymers have been recognised as useful for the treatment of hypercholesterolaemia, and it is now proven that reducing serum cholesterol with bile acid sequestrants has a beneficial effect on protecting against the occurrence of coronary heart disease.

The polystyrene polymers known in the art to have such sequestering activity are, in general, those bearing a di- or triloweralkyl ammonium group, such as a trimethylammonium group. For example, GB 1286949 discloses a series of macroporous polystyrene polymers having 5-20% cross-link, and GB 1579490 discloses a series of microporous polymers having 8-20% cross-link. In addition, GB 2026501 discloses a series of, inter alia, polystyrene polymers which are said to have particular water absorption capacities, i.e. 69-73% by weight of polymer weight. In each of the foregoing, the polystyrene polymers bear di- or triloweralkyl ammonium groups, in particular a trimethylammonium group.

One particular agent based on a polystyrene polymer which is currently used to lower serum cholesterol levels in humans by binding bile acids in the intestinal tract is cholestyramine (GB 929391). Cholestyramine is a cross-linked anion exchange polystyrene polymer bearing an ionisable trimethylammonium group bound to the polymer backbone. However, the use of this agent is associated with a number of undesirable side-effects, for example, it is unpalatable and must be taken in large doses (up to 36 g per day) and causes, in some cases, bloating, constipation and other gut side-effects. In addition, its ability to bind bile acids is inefficient with respect to the amounts of polymer which it is necessary to use.

It is the object of the present invention to provide compounds which overcome the disadvantages of this known sequestering agent and provide improved bile acid sequestering agents which are useful for lowering serum cholesterol levels in humans.

The present invention therefore provides in a first aspect, polystyrene polymers of structure (I):

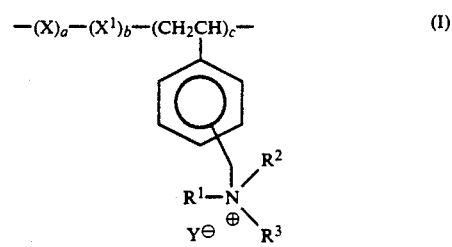

in which,

X is a comonomer unit;
$X^1$ is a cross-linking unit;
$R^1$ is a saturated or unsaturated $C_6$ to $C_{20}$ alkyl group;
$R^2$ and $R^3$ are the same or different and are each $C_{1-4}$alkyl;
$Y^-$ is a physiologically acceptable counter ion;
a, b and c are numbers which indicate the relative molar percentages of the units present in a random distribution in said polymer, (b) being from about 0.5 to about 10 molar percent, and (c) being from about 30 to about 99 molar percent; provided that when X is styrene, $X^1$ is other than divinylbenzene;

Suitably X is a co-monomer unit. Preferably X is styrene, an alkyl methacrylate of structure (i) or an alkylstyrene of structure (ii)

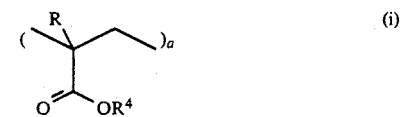

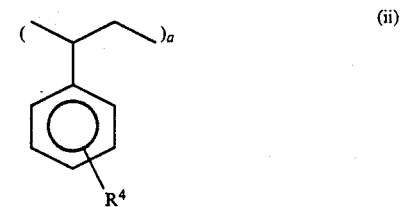

in which a is as described for structure (I), R is $C_{1-4}$alkyl and $R^4$ is $C_{1-20}$alkyl. In such groups, R is preferably methyl, and $R^4$ is preferably $C_{6-12}$alkyl, especially n-octyl.

Suitably, $X^1$ is a cross-linking unit i.e. a unit which provides a random distribution of cross-links between chains of polymers. Preferred such units include, for example, divinylbenzene, and alkylene glycol bis methacrylates of structure (iii)

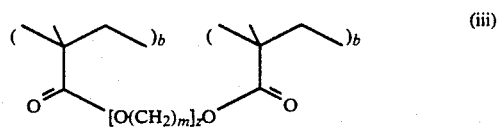

in which m is 2 to 6, z is 1 to 4 and (b) comprises from about 0.5 to about 10 molar percent of said polymer.

Preferred cross-linking units of structure (iii) include, for example ethylene glycol bis methacrylate, (z=1, m=2); 1,6-hexanediol bis methacrylate (z=1, m=6)

and tetramethyleneglycol bis methacrylate ($z=4$, $m=2$).

Divinylbenzene cross-linking units are of structure (iv)

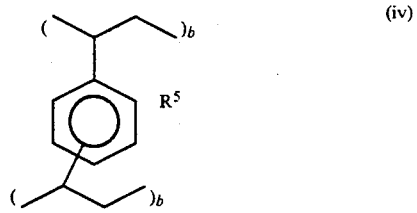

in which $R^5$ is hydrogen or $CH_2NR^1R^2R^3Y^-$ in which $R^1$ to $R^3$ and $Y^-$ are as described for structure (I). It will be appreciated by those skilled in the art that polymers of structure (I) may contain mixtures of such divinylbenzene units i.e. a proportion in which $R^5$ is hydrogen and a proportion in which $R^5$ is

Similarly, the polymers of structure (I) may also contain mixtures of comonomer units in the same structure, for example, styrene units along with alkyl styrene units of structure (ii). The general formula (I) is intended to cover polymers in which such mixtures of the groups X and $X^1$ occur.

Suitably, $R^1$ is a saturated or unsaturated $C_6$ to $C_{20}$ alkyl group. More suitably $R^1$ is a saturated $C_6$ to $C_{20}$ alkyl group. Preferably $R^1$ is a saturated $C_8$ to $C_{14}$ alkyl group; most preferably a $C_{12}$ alkyl group, in particular an unbranched $C_{12}$ alkyl group.

Suitably the groups $R^2$ and $R^3$ are the same or different and are each $C_{1-4}$alkyl; preferably they are the same; most preferably $R^2$ and $R^3$ are both methyl.

Suitably (b) is from about 0.5 to about 10 molar percent of said polymer, preferably (b) is from about 1 to about 8 molar percent of said polymer; most preferably from about 1 to about 4 molar percent.

Suitably $Y^-$ is a physiologically acceptable counter ion such as a sulphate, bicarbonate, carbonate, formate, acetate, sulphonate, propionate, malonate, succinate, malate, tartrate, citrate, maleate, fumarate, ascorbate, glucuronate, phosphate, or halide, or the anion of an amino acid such as aspartic or glutamic acid. More suitably $Y^-$ is a phosphate, sulphate or a halide ion; preferably a halide ion, in particular chloride.

The polystyrene polymers of the present invention are also characterised by their total exchange capacity i.e. the theoretical maximum capacity of the polymer if each counter ion were to be exchanged with bile acid. In this specification the total exchange capacity is defined in terms of the number of milliequivalents of counter ion per gram of dry weight of polymer.

Suitable total exchange capacities are in the range of, for example where the counter ion $X^-$ is a halide ion such as chlorine, from 1.5 to 3.5 meq $Cl^-$ per gram of polymer. Preferred within this range are polymers having a total exchange capacity of between 2 and 3 meq $Cl^-$/gram of polymer.

In addition, it is to be noted that the approximate molar percentages (a), (b) and (c) are calculated from the monomer mixture or, in some instances (c) from microanalytical data.

It is to be noted that the term 'bile acid' when used herein shall be taken to include bile acids, bile salts and conjugates thereof.

The polystyrene polymers of the present invention can be prepared by processes analogous to those known in the art for example by:

(a) reaction of a polymer of structure (II)

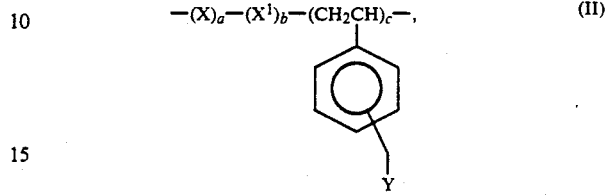

in which X, $X^1$, a, b and c are as described for structure (I) and Y is a group displaceable by an amine, with an amine of structure $R^1R^2R^3N$ (III) in which $R^1$ to $R^3$ are as described for structure (I);

(b) reaction of a compound of structure (IV)

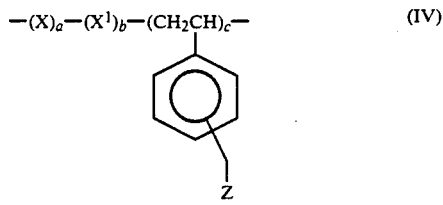

in which X, $X^1$, a, b and c are as described for structure (I) and Z is $NR^1R^2$ or $NR^2R^3$ in which $R^1$ to $R^3$ are as described for structure (I), with a compound of structure $R^4Y$ (V) in which $R^4$ is a $C_{1-4}$alkyl group when Z is $NR^1R^2$ or a saturated or unsaturated $C_{6-20}$ alkyl group when Z is $NR^2R^3$, and Y is a group displaceable by an amine.

The reaction between a polymer of structure (II) and an amine of structure (III) can be carried out in a suitable solvent at elevated temperature. Suitable solvents include for example, a $C_{1-4}$alkanol, N-methylpyrrolidone, sulpholane, dimethylformamide, nitromethane or tetrahydrofuran. Preferably the reaction is carried out in N-methylpyrrolidone at a temperature of between about 50° and 80° for up to 24 hours or until the reaction is complete.

The reaction between a polymer of structure (IV) and a compound of structure (V) can be carried out in a suitable inert solvent such as a $C_{1-4}$alkanol, nitromethane, sulpholane, N-methylpyrrolidone, dimethylformamide or tetrahydrofuran at elevated temperature.

The intermediate polymers of structure (II) are available commercially or can be prepared from readily available materials by methods known to those skilled in the art. For example polymers of structure (II) in which Y is chlorine can be prepared by reaction of chloromethylstyrene, styrene and divinyl benzene in an aqueous suspension comprising polyvinyl alcohol in the presence of an initiator such as AIBN at elevated temperature.

Alternatively, the intermediate polymers of structure (II) can be prepared directly from polystyrene by methods analogous to those known in the art, for example where Y is chlorine by chloromethylation of polystyrene.

Certain intermediates of structure (IV) are novel and form a further aspect of the invention namely compounds of structure (IVA)

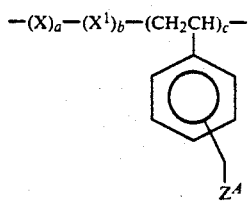

in which X, $X^1$, a, b and c are as described for structure (I) and $Z^A$ is $NR^1R^2$ or $NR^1R^3$ in which $R^1$ to $R^3$ are as described for structure (I).

The intermediate polymers of structure (IV) can be prepared from the polymers of structure (II) by reaction with an amine of structure $R_2NH$ in which $R_2$ is $R^1R^2$ or $R^2R^3$ under the same or similar conditions as indicated for the reaction of a compound of structure (II) and a compound of structure (III).

Alternatively the intermediate polymers of structure (IV) can be prepared by polymerisation of styrene, divinylbenzene and a compound of structure (V)

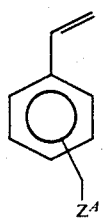

in which $Z^a$ is as defined in structure (IVA), under standard polymerisation conditions. For example, polymerisation can be carried out in an aqueous suspension comprising, for example, polyvinyl alcohol in the presence of an initiator at elevated temperature. Suitable initiators include, for example, AIBN.

The intermediate compounds of structure (V) can be prepared by reaction of an amine of structure $R_2NH$ in which $R_2$ is $R^1R^2$ or $R^1R^3$ with a corresponding compound of structure (V) in which $Z^a$ is a group displaceable by an amine.

The polystyrene polymers of structure (I) have been found to bind bile acids in in vitro experiments and in in vivo animal models they have been found to increase the amount of bile acids detectable in the faeces. In particular, when compared to the known sequestrants e.g. cholestyramine, the polymers of structure (I) have surprisingly been found to have an unexpected profile of activity which is thought will provide advantages over the known compounds in the lowering of serum cholesterol levels in animals, in particular humans. More specifically, in in vitro experiments, when compared to cholestyramine the compounds of structure (I) have been found to bind comparable amounts of bile acid per gram of polymer (at physiological concentrations of bile acids), and to bind the bile acid more strongly i.e., the bile acids have been found to dissociate more slowly from the compounds of the invention. It is expected that compounds having such qualities will be able to achieve significant lowering of plasma cholesterol levels at much lower dosages than has hitherto been possible with known sequestrants (currently given at up to 36 g/day).

As indicated earlier it is recognised that removal of bile acids from the intestinal tract in this way lowers serum cholesterol levels and also has a beneficial effect on protecting against atherosclerosis and its dependent clinical conditions. The present invention therefore provides in a further aspect, polystyrene polymers of structure (I) for use in therapy, in particular for the lowering of serum cholesterol levels in mammals, including humans. In addition the polymers of structure (I) are expected to be of use in protecting against atherosclerosis and its sequelae, and for example in the treatment of pruritus and diarrhoea.

In view of the foregoing the present invention also provides a method of lowering serum cholesterol levels in mammals which comprises administering to a mammal in need thereof an effective serum cholesterol lowering amount of a polystyrene polymer of structure (I); and a method of protecting against atherosclerosis.

When used in therapy in the methods of the invention, the polystyrene polymers of structure (I) are in general administered in a pharmaceutical composition.

In a still further aspect of the present invention there is therefore provided a pharmaceutical composition comprising a polystyrene polymer of structure (I) in association with a pharmaceutically acceptable carrier.

The compositions of the present invention can be prepared by techniques well known to those skilled in the art of pharmacy and include all those known for the formulation of polystyrene polymers for human use.

The polymers are preferably administered as formulations in admixture with one or more conventional pharmaceutical excipients which are physically and chemically compatible with the polymer, which are non-toxic, are without deleterious side-effects but which confer appropriate properties on the dosage form.

In general, for liquid formulations, aqueous based pharmaceutically acceptable carriers such as water itself or aqueous dilute ethanol, propylene glycol, polyethylene glycol or glycerol or sorbitol solutions are preferred.

Such formulations can also include preservatives and flavouring and sweetening agents such as sucrose, fructose, invert sugar, cocoa, citric acid, ascorbic acid, fruit juices etc. In general, digestible oil or fat based carriers should be avoided or minimised as they contribute to the condition sought to be alleviated by use of the polymers. They are also subject to absorption by the polymers during prolonged contact, thus reducing the capacity of the polymer to absorb bile acids after administration.

The polymers can also be prepared as 'concentrates', for dilution prior to administration, and as formulations suitable for direct oral administration. They can be administered orally ad libitum. on a relatively continuous basis for example by dispersing the polymer in drinks or food.

Preferably, the polymers are administered in tablet form or in gelatin capsules containing solid particulate polymer or a non-aqueous suspension of solid polymer containing a suitable suspending agent. Suitable excipients for such formulations will be apparent to those skilled in the art and include, for example, for tablets and capsules lactose, microcrystalline cellulose, magnesium stearate, povidone, sodium starch glycollate and starches; and for suspensions in capsules, polyethylene glycol, propylene glycol and colloidal silicon dioxide.

Preferably the polymer is administered in unit dosage form, each dosage unit containing preferably from 0.3 g to 1 g of polymer.

The daily dosage regimen for an adult patient may be, for example, a total daily oral dose of between 1 and 10 g, preferably 1-5 g, the compound being administered 1 to 4 times a day depending on the size of individual dosage units. Suitably the compound is administered for a period of continuous therapy of one month or more sufficient to achieve the required reduction in serum cholesterol levels.

In addition the polymers of the present invention can be co-administered (together or sequentially) with further active ingredients such as HMGCoA reductase inhibitors and other hypocholesterolaemic agents, and other drugs for the treatment of cardiovascular diseases.

The following data and examples indicate the properties and preparation of the polymers of the present invention. Temperatures are recorded in degrees celsius. The exchange capacity of the ammonium substituted polymers was determined by elemental analysis and/or potentiometric titration of chloride ion. Figures quoted are expressed as milliequivalents of exchangeable chloride ion per gram of dry polymer weight.

Chloromethylstyrene was used as a 60:40 m:p mixture and was washed free of inhibitor before use.

Divinylbenzene (DVB) was used as a 55% mixture with ethylstyrene and the weights given are that of the mixture. The percent cross-link given is based on the percent of divinylbenzene (not the mixture) calculated to be in the monomer mixture. The molar percent of divinylbenzene (b) quoted is based on the molar percent of DVB in the monomer mixture.

EXAMPLE 1

(a) Chloromethylstyrene (32.0 g), ethyl methacrylate (17.1 g), divinylbenzene (0.91 g) and azobisisobutyronitrile (AIBN) (0.5 g) were mixed to give a solution and added to a solution of poly(vinylalcohol) (mw 125,000) (1.0 g) in distilled water (500 ml). The mixture was stirred at 80° under an atmosphere of nitrogen at such a rate as to maintain the monomers in suspension. After 7 hours, the stirring was stopped and the mixture poured into distilled water. The resin formed was washed by decantation with cold and hot water, acetone, tetrahydrofuran, and acetone. Drying under reduced pressure gave an approximately 1% (w/w) ($\mu$1.05 molar %) cross-linked chloromethyl-substituted polystyrene resin (chloromethylstyrene-ethyl methacrylate-divinylbenzene co-polymer) containing 3.85 meq Cl/g (22.5 g). This was sieved and the 53-106 $\mu$m fraction used (14.85 g).

(b) The above polymer (4.0 g) was suspended in dimethylformamide (DMF) (40 ml). N,N-Dimethyldodecylamine (10.24 g) was added and the mixture was heated at 65° for 24 hours. After cooling, the mixture was passed through a 53 micron sieve. The retained beads were washed with methanol and diethyl ether and dried under vacuum to give N,N-dimethyl-N-dodecylammoniomethyl-substituted polystyrene, chloride salt, (N,N-dimethyl-N-dodecylammoniomethylstyrene-ethyl methacrylate-divinylbenzene co-polymer, chloride salt), (6.3 g) containing 2.08 meq Cl$^-$/g.

EXAMPLE 2

(a) Chloromethylstyrene (32.5 g), styrene (17.0 g), ethyleneglycol bismethacrylate (0.5 g) and azobisisobutyronitrile (0.5 g) were polymerised as in Example 1 to give an approximately 1% (w/w) ($\mu$0.67 molar %) cross-linked chloromethyl-substituted polystyrene resin (chloromethylstyrene-styrene-ethyleneglycol bismethacrylate co-polmer) containing 3.93 meq Cl/g (28.0 g, 53-106$\mu$ after sieving).

(b) The above polymer (5.0 g) was treated with N,N-dimethyldodecylamine (12.8 g) in DMF (140 ml) as in Example 1 to give N,N-dimethyl-N-dodecylammoniomethyl-substituted polystyrene, chloride salt, (N,N-dimethyl-N-dodecylammoniomethylstyrene-styrene-ethyleneglycol bismethacrylate co-polymer, chloride salt) as white polymer beads (7.9 g) (2.12 meq Cl$^-$/g).

EXAMPLE 3

(a) Chloromethylstyrene (32.0 g), ethyl methacrylate (17.5 g), ethyleneglycol bismethacrylate (0.5 g) and AIBN (0.5 g) were polymerised as in Example 1 to give an approximately 1% (w/w) ($\mu$0.69 molar %) cross-linked chloromethyl-substituted polystyrene resin (chloromethylstyrene-ethyl methacrylate-ethyleneglycol bismethacrylate co-polymer) containing 3.88 meq Cl/g (17.2 g, 53-106 $\mu$m after sieving).

(b) The above polymer (5.0 g) was reacted with N,N-dimetyldodecylamine (17.0 g) as in Example 1 to give the corresponding N,N-dimethyl-N-dodecylammoniomethyl-substituted polystyrene, chloride salt (N,N-dimethyl-N-dodecylammoniomethylstyrene-ethyl methacrylate-ethyleneglycol bismethacrylate co-polymer, chloride salt) as white polymer beads, (8.6 g) (2.10 meq Cl$^-$/g).

EXAMPLE 4

(a) Aluminium chloride (84.3 g) was suspended in dry dichloromethane (250 ml), cooled to 10° and acetyl chloride (49.6 g) added over 5 minutes at 10°-20°. The mixture was stirred at room temperature for 30 minutes then octylbenzene (100.3 g) was added over 30 minutes to the resulting solution with slight cooling to keep the temperature at 20°-22°. After the addition the mixture was stirred at room temperature for 3.5 hours then poured onto ice (1 kg). The phases were separated and the dichloromethane solution was washed with water, dilute sodium hydroxide and water, and dried over magnesium sulphate. Evaporation of the solvent gave magnesium sulphate. Evaporation of the solvent gave 4-acetyl-1-octylbenzene as an oil (117.3 g, 96%).

(b) 4-Acetyle-1-octylbenzene (177.0 g) was dissolved in ethanol (800 ml), cooled to 10° and sodium borohydride (38.2 g) was added in portions over 5 minutes. The mixture was stirred at room temperature for 20 hours. The solvent was evaporated and the residue was partitioned between water and diethyl ether. The diethyl ether solution was washed with water, dilute hydrochloric acid and water, dried over magnesium sulphate and evaporated to give 4-(1-hydroxyethyl)-1-octylbenzene as a colourless oil which solidified on cooling (116.3 g, 98%).

(c) 4-(1-Hydroxyethyl)-1-octylstyrene (113.7 g) was heated at 200° under vacuum (10 mmHg) for 0.5 hour. The resulting oil was partitioned between water and diethyl ether and the diethyl ether solution was washed with water, dilute sodium hydroxide and water, dried over magnesium sulphate and evaporated to an oil. This oil was distilled to give 4-octylstyrene as a colourless oil (48.2 g, 46%), bp 106°-8°/0.03 mmHg.

(d) Chloromethyl styrene (13.0 g), 4-octylstyrene (3.69), divinylbenzene (0.31 g) and azobisisobutyronitrile (0.2 g) were polymerised in solution of poly(vinyl alcohol) (MW 125,000) (1.0 g) in distilled water (250 ml) as in Example 1 to give an approximately 1% (w/w) (μ1.26 molar %) cross-linked chloromethyl-substituted polystyrene resin (chloromethyl-styrene-4-octystyrene-divinylbenzene co-polymer).

(e) The above polymer (4.0 g) was reacted with N,N-dimethyldodecylamine (10.24 g) as in Example 1 to give the corresponding N,N-dimethyl-N-dodecylammoniomethyl-substituted polystyrene, chloride salt, (N,N-dimethyl-N-dodecylammoniomethylstyrene-4-octylstyrene-divinylbenzene co-polymer, chloride salt) as white polymer beads, (6.6 g) (2.08 meq Cl$^-$/g).

Bile Acid Binding Assay

Test compound (150 mg) was equilibrated with 5 mM sodium glycocholate (30 ml)—a typical physiological concentration—in Krebs' buffer for 3 hours. The compound was separated by centrifugation and the total bound determined by subtraction of the amount in the supernatant from the total bile acid used. Bile acid dissociation was measured by resuspending the compound in Krebs' buffer, shaking and sampling the mixture through a filter at several time points up to 20 minutes. Radioactivity and hence bile acid dissociated was determined in the filtrate (Table I).

TABLE 1

| Example | GC Bound (mmoles/g) | | % Dissociation |
|---|---|---|---|
| | t = 0 | t = 2 min | |
| Cholestyramine | 0.76 | 0.42 | 45 |
| 1 | 0.85 | 0.67 | 21 |
| 2 | 0.74 | 0.66 | 11 |
| 3 | 0.80 | 0.72 | 10 |
| 4 | 0.68 | 0.60 | 12 |

What is claimed is:

1. A pharmaceutical composition comprising a polystyrene polymer of structure I

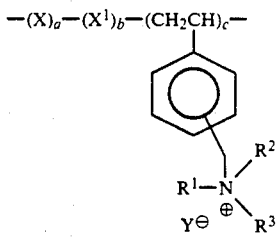

in which,
X is a comonomer unit;
$X^1$ is a cross-linking unit;
$R^1$ is a saturated or unsaturated $C_8$ to $C_{20}$ alkyl group;
$R^2$ and $R^3$ are the same or different and are each $C_{1-4}$ alkyl;
$Y^-$ is a physiologically acceptable counter ion;
a, b and c are numbers which indicate the relative molar percentages of the units present in a random distribution in said polymer, (b) being from about 0.5 to about 10 molar percent, and (c) being from about 30 to about 99 molar percent; provided that when X is styrene, $X^1$ is other than divinylbenze, in association with a pharmaceutically acceptable carrier, where the active ingredient is the polymer.

2. A pharmaceutical composition according to claim 1, in which, in the compound of structure (I) $R^1$ is a saturated $C_8$ to $C_{14}$ alkyl group and $R^2$ and $R^3$ are each methyl.

3. A pharmaceutical composition according to claim 2 in which, in the compound of structure (I) (b) is from about 1 to about 4 molar percent.

4. A pharmaceutical composition according to claim 3 wherein the compound of structure (I) is an N,N-dimethyl-N-dodecylammoniomethylstyrene-ethyl methacrylate-divinylbenzene, derivative.

5. A pharmaceutical composition according to claim 3 wherein the compound of structure (I) is an N,N-dimethyl-N-dodecylammoniomethylstyrene-styrene-ethyleneglycol bismethacrylate derivative.

6. A pharmaceutical composition according to claim 3 wherein the compound of structure (I) is an N,N-dimethyl-N-dodecylammoniomethylstyrene-ethyl methacrylate-ethyleneglycol bismethacrylate derivative.

7. A pharmaceutical composition according to claim 3 wherein the compound of structure (I) is an N,N-dimethyl-N-dodecylammoniomethylstyrene-4-octylstyrene-divinylbenzene derivative.

8. A method of treatment of hypercholesterolaemia in mammals, including humans which comprises administering to a subject in need thereof an effective amount of a composition as described in claim 1.

9. A method according to claim 8 wherein the active ingredient of the composition comprises an N,N-dimethyl-N-dodecylammoniomethylstyrene-ethyl methacrylate-divinylbenzene derivative.

10. A method according to claim 8 wherein the active ingredient of the composition comprises an N,N-dimethyl-N-dodecylammoniomethylstyrene-styrene-ethyleneglycol bismethacrylate derivative.

11. A method according to claim 8 wherein the active ingredient of the composition comprises an N,N-dimethyl-N-dodecylammoniomethylstyrene-ethyl methacrylate-ethyleneglycol bimethacrylate derivative.

12. A method according to claim 8 wherein the active ingredient of the composition comprises an N,N-dimethyl-N-dodecylammoniomethylstyrene-4-octylstyrene-divinylbenzene derivative.

* * * * *